United States Patent
Gross et al.

[19]

[11] Patent Number: 6,099,504
[45] Date of Patent: Aug. 8, 2000

[54] PRE-FILLED INJECTION DELIVERY DEVICE

[75] Inventors: Joseph Gross, Moshav Mazor; Gilad Lavi, Holon, both of Israel; Izrail Tsals, Sudbury, Mass.

[73] Assignee: Elan Corporation, plc, Dublin, Ireland

[21] Appl. No.: 09/176,439

[22] Filed: Oct. 21, 1998

[51] Int. Cl.$^7$ ............................ A61M 37/00; A61M 5/32
[52] U.S. Cl. ........................ 604/140; 604/145; 604/198
[58] Field of Search .................. 604/93, 110, 140, 604/141, 143, 145, 148, 171, 198, 200

[56] References Cited

U.S. PATENT DOCUMENTS

| | | | |
|---|---|---|---|
| 3,811,441 | 5/1974 | Sarnoff .................. | 128/218 DA |
| 3,889,673 | 6/1975 | Dovey et al. ............. | 128/215 |
| 3,895,633 | 7/1975 | Bartner et al. ........... | 128/218 DA |
| 4,031,890 | 6/1977 | Homan .................. | 128/215 |
| 4,328,802 | 5/1982 | Curley et al. ........... | 128/272.1 |
| 4,427,039 | 1/1984 | Brooks et al. ........... | 141/20 |
| 4,468,220 | 8/1984 | Willbanks ............... | 604/133 |
| 4,624,393 | 11/1986 | Lopez .................. | 222/83.5 |
| 4,645,073 | 2/1987 | Homan .................. | 206/219 |
| 4,713,061 | 12/1987 | Tarello et al. .......... | 604/200 |
| 4,747,839 | 5/1988 | Tarello et al. .......... | 604/240 |
| 4,838,857 | 6/1989 | Strowe et al. ........... | 604/67 |
| 4,900,307 | 2/1990 | Kulli .................. | 604/110 |
| 4,904,242 | 2/1990 | Kulli .................. | 604/110 |
| 4,927,414 | 5/1990 | Kulli .................. | 604/110 |
| 4,929,241 | 5/1990 | Kulli .................. | 604/263 |
| 4,938,742 | 7/1990 | Smits .................. | 604/67 |
| 4,941,880 | 7/1990 | Burns .................. | 604/143 |
| 4,969,874 | 11/1990 | Michel et al. .......... | 604/140 |
| 5,013,303 | 5/1991 | Tamari et al. .......... | 604/140 |
| 5,106,374 | 4/1992 | Apperson et al. ........ | 604/140 |
| 5,163,909 | 11/1992 | Stewart ................ | 604/140 |
| 5,169,388 | 12/1992 | McPhee ................. | 604/90 |
| 5,304,128 | 4/1994 | Haber et al. ........... | 604/68 |
| 5,342,319 | 8/1994 | Watson et al. .......... | 604/180 |
| 5,411,489 | 5/1995 | Pagay et al. ........... | 604/218 |
| 5,433,704 | 7/1995 | Ross et al. ............ | 604/67 |
| 5,460,611 | 10/1995 | Alexander .............. | 604/110 |
| 5,462,525 | 10/1995 | Srisathapat et al. ..... | 604/67 |
| 5,472,430 | 12/1995 | Vallincourt et al. ..... | 604/198 |
| 5,478,316 | 12/1995 | Bitidinger et al. ...... | 604/135 |
| 5,540,665 | 7/1996 | Mercado et al. ......... | 604/145 |
| 5,545,143 | 8/1996 | Fischell ............... | 604/180 |
| 5,611,779 | 3/1997 | Saito et al. ........... | 604/156 |
| 5,713,872 | 2/1998 | Feuerborn et al. ....... | 604/192 |
| 5,746,215 | 5/1998 | Manjarrez .............. | 128/763 |
| 5,746,714 | 5/1998 | Salo et al. ............ | 604/68 |

FOREIGN PATENT DOCUMENTS

| | | | |
|---|---|---|---|
| 0 201 170 | 12/1986 | European Pat. Off. ......... | C09K 5/06 |
| 0 557 559 | 9/1993 | European Pat. Off. ....... | A61M 5/315 |
| 2461 272 | 1/1976 | Germany ................ | A61M 5/20 |
| WO 94/26329 | 11/1994 | WIPO .................. | A61M 5/155 |
| WO 96/32974 | 10/1996 | WIPO .................. | A61M 5/20 |
| WO 99/03521 | 1/1999 | WIPO .................. | A61M 5/30 |

*Primary Examiner*—Mark O. Polutta
*Assistant Examiner*—Michael J. Hayes
*Attorney, Agent, or Firm*—Kathleen L. Maher

[57] ABSTRACT

A syringe (10) comprises a barrel (11) containing an internal cylindrical body (12) containing a liquid (14) and communicating with a delivery needle (15). The needle (15) is covered before use by a removable sheath (16), and after the sheath (16) is removed, the needle (15) is concealed by a displaceable sleeve (20). In use the sleeve (20) is pressed against the skin by applying pressure while holding the barrel (11). The sleeve (20) is thereby retracted into the barrel (11) allowing the needle (15) to penetrate the skin. The movement of the sleeve (20) also activates a gas generator (17) which expels the liquid (14) from the needle (15). When delivery is complete and the syringe (10) is taken from the skin, a coil spring (22) moves the sleeve (20) back to the starting position again concealing the needle (15). The coil spring (22) is torsionally biased before use and causes a rotational movement of the sleeve (20) relative to the barrel (11) when the sleeve (20) moves into and out of the barrel (11). This rotational movement engages a locking mechanism which prevents further movement of the sleeve (20) and thereby permanently conceals the needle (15).

30 Claims, 6 Drawing Sheets

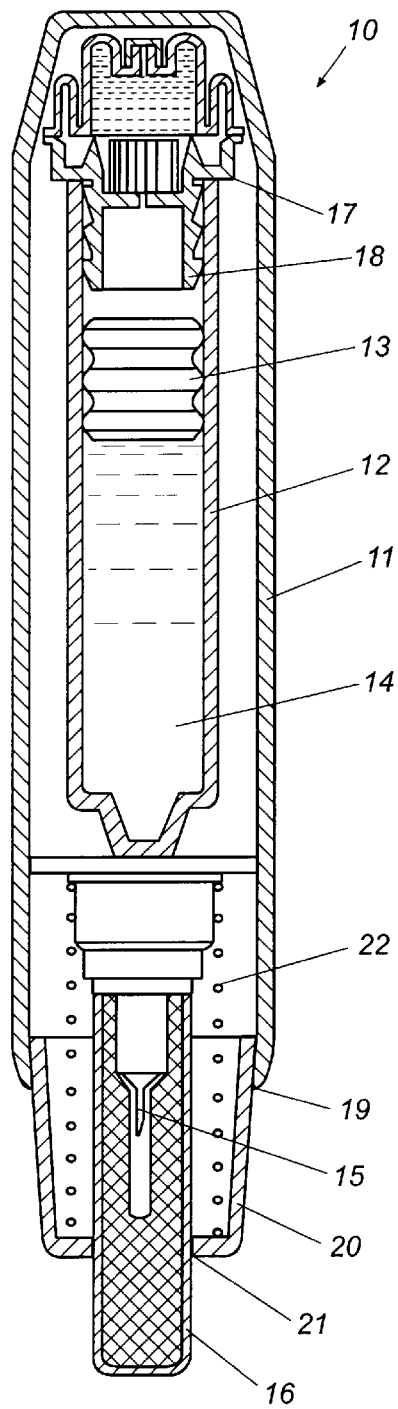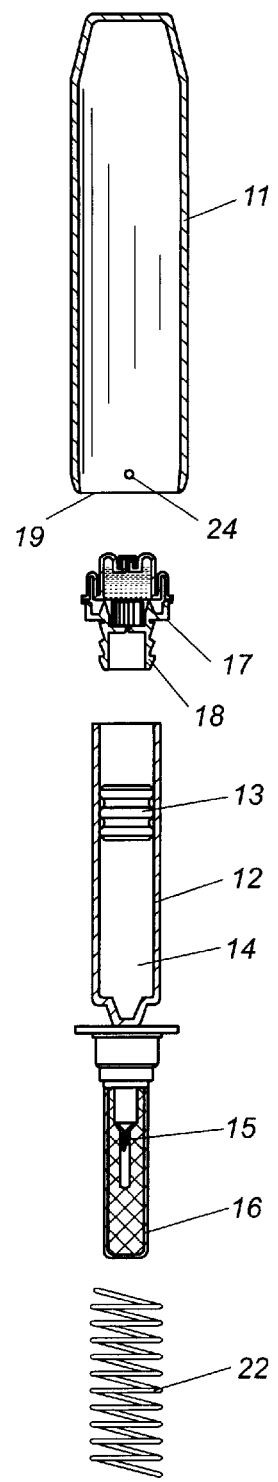
Fig. 1
Fig. 2

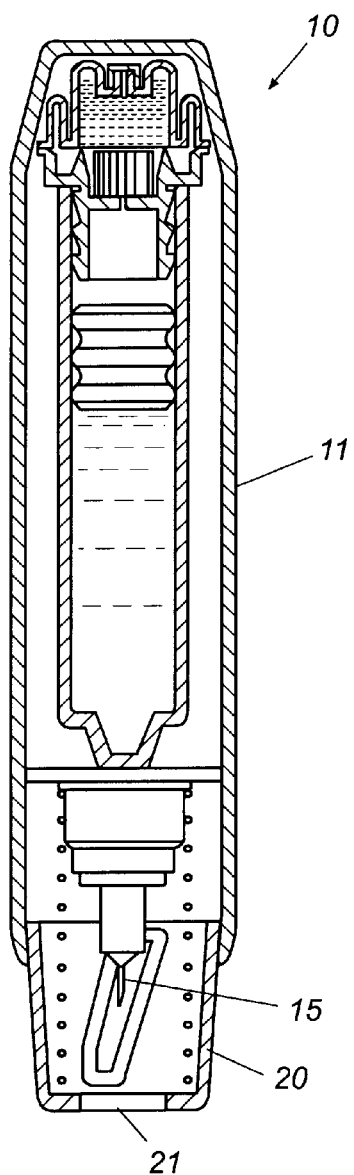
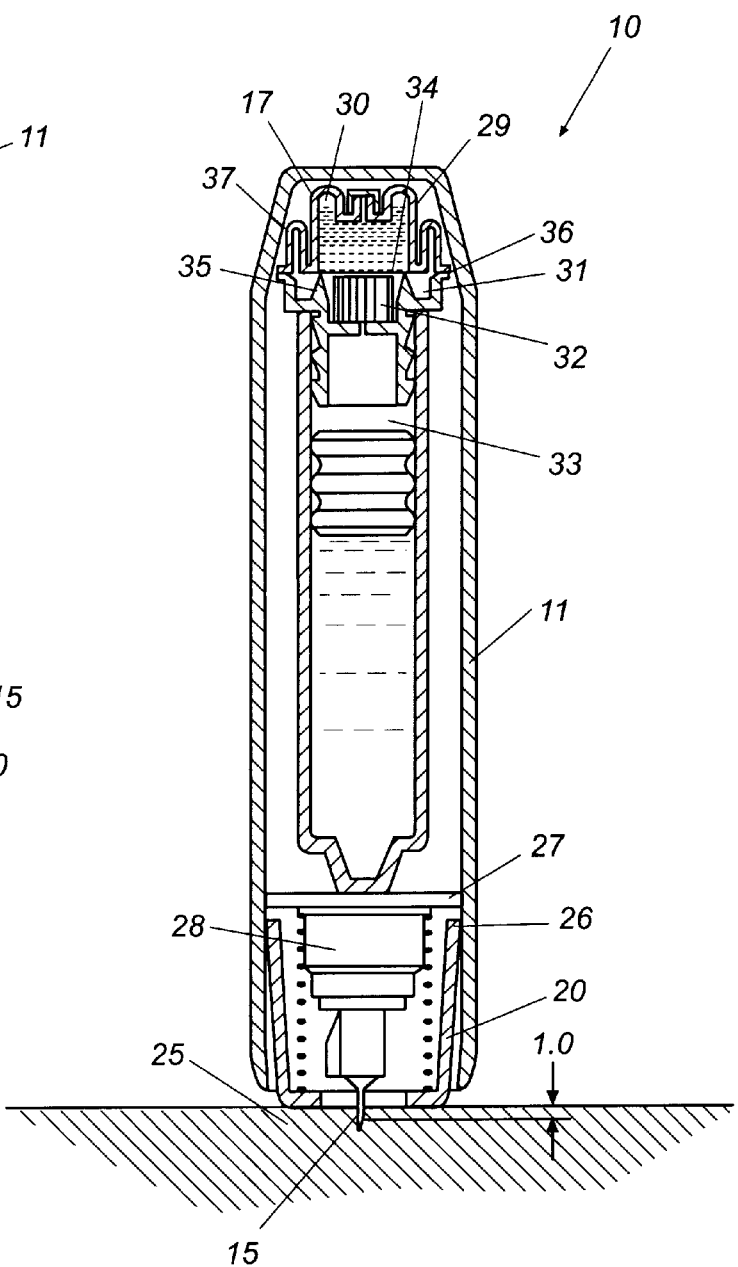
Fig. 3
Fig. 4

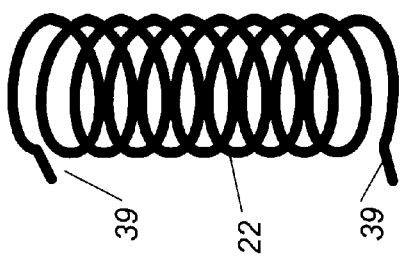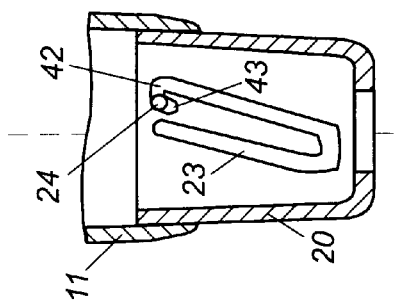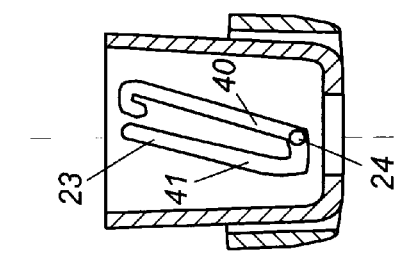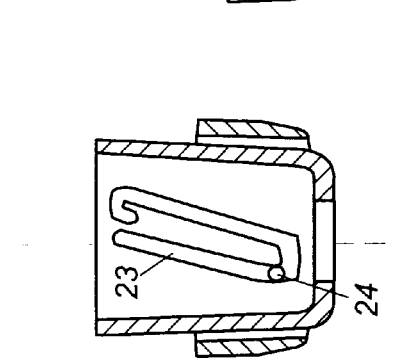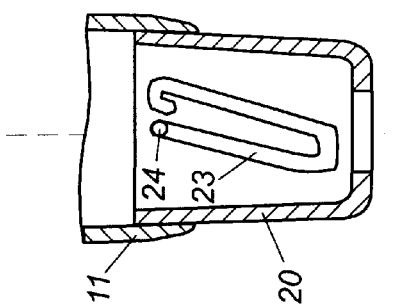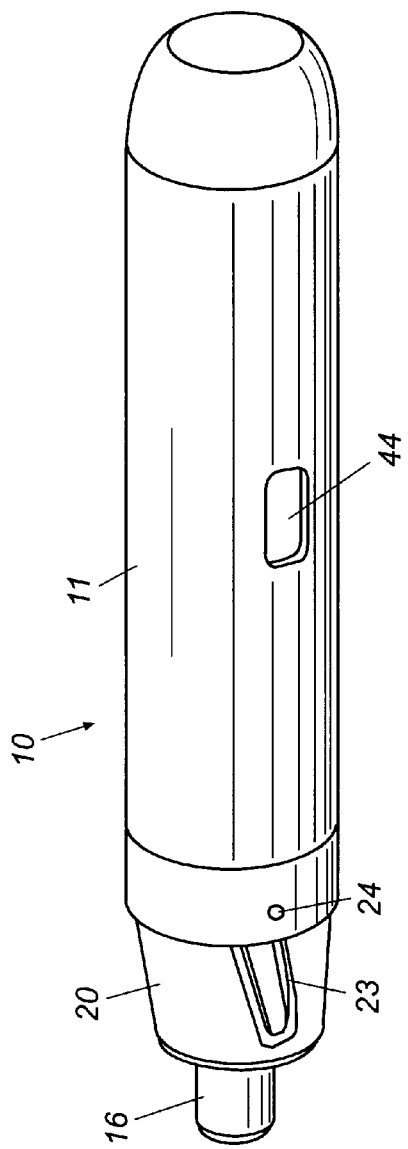

PRE-FILLED INJECTION DELIVERY DEVICE

This invention relates to automatic syringes, particularly for the delivery of drugs and other substances to human and animal subjects.

The problems associated with conventional syringes arise from the fact that they are unsuitable for use by untrained users. They are liable to cause injury and infection if not disposed of correctly, are available for re-use by drug addicts if not disposed of properly, and they are painful to the patient if not used correctly. Many patients are "needle-phobic" and thus are extremely reluctant to use syringes regardless of the objective pain caused by a syringe even when used correctly.

A In order to combat user compliance problems due to a fear of needles, a number of needleless syringe designs have been proposed. Such syringes deliver a drug to the subject by forcing the drug through the skin of the subject under air pressure.

The pressure required for such delivery is quite high—of the order of 6 atmospheres (approximately 600 kPa). This in itself gives rise to problems, since it leads to vials being broken occasionally under high pressure. It also means that the syringe must be primed before use, since a pre-filled ready-to-use syringe cannot be stored under such high pressure over a shelf life of months or years. Thus, the user or a physician or nurse is required to prepare the syringe before it can be used, which detracts from its attractiveness for self-administration.

A further problem which arises in needleless delivery is that the high pressure is primarily required to drive the drug through the stratum corneum layer of the skin. Underlying layers of the skin, and the subcutaneous tissue itself present relatively little resistance to the passage of the high-velocity powder. Because different patients have different skin types and thicknesses, and because the thickness and penetrability of the skin varies widely over a single patient's body, the level of the needleless syringe delivery pressure must be regulated to drive the drug correctly past the stratum corneum.

A failure to correctly regulate the level of the driving pressure may result in an incorrect level of delivery due to insufficient levels of drug passing the stratum corneum, or due to the drug being delivered past the target tissue to the wrong type of tissue. For example if the delivery pressure is too high the drug may be delivered to the bone surface underlying the delivery region.

A further problem with needleless syringes is that they are considerably more bulky than conventional syringes due to the complex delivery mechanism and the thickness of walls required to contain the pressurised gas.

Alternative drug delivery devices are known which correctly deliver the drug in an automatic fashion but have certain disadvantages when compared to syringes. For example, our own WO-A-97/21457 discloses a drug delivery device containing a reservoir in communication with a needle, and a gas generator adapted to drive a medicament from the reservoir to the subject via the needle.

The device of WO-A-97/21457 is adapted to be affixed to the skin by an adhesive coating (covered before use by a release liner). When attached to the skin and actuated, delivery is automatic. After completion of delivery, the device is pulled away from the skin, causing the needle to be concealed by means of a displaceable cover, before the device is disposed of.

The device disclosed in WO-A-97/21457 is bulkier than that of a syringe which would deliver the same volume of drug, due to the configuration of the housing and the displaceable cover, which must provide a surface of sufficient surface area to be attached to the skin.

Additionally, when compared with a syringe, more steps are involved in effecting a suitable injection with the device disclosed in WO-A-97/21457 (for example, the release liner must be peeled away before the device can be operated). This makes the device less attractive to patients in need of an immediate injection because of the longer time needed to administer individual injections.

The above-mentioned prior art device while simpler than a needleless injector, is still somewhat complex as regards the automatic actuation of the gas generator and the locking snap mechanism which ensures that the needle is properly concealed by the displaceable cover before and after use. Added complexity results in higher costs and a greater possibility of device malfunction.

The present invention aims to overcome these and other disadvantages of the prior art and provide a syringe which is preferable to conventional syringes as well as to needleless injectors or automatic infusion pumps.

The invention provides a syringe comprising:

a) a barrel having a liquid drug reservoir therein;

b) a delivery needle mounted on the first end of the barrel;

c) a gas generator located at the second end of the barrel, the gas generator in communication with the reservoir when the gas generator is activated, so as to drive a liquid from the reservoir through the needle;

d) gas generation activation means; and e) a sleeve resiliently mounted on the first end of the barrel between a first position where the tip of the needle is concealed by the sleeve to a second position where the tip of the needle is revealed, f) whereby when the sleeve is placed against an injection site and the barrel is moved toward the injection site, the sleeve is caused to move from the first position to the second position, and the needle is caused to penetrate the injection site, such that activation of the gas generator drives a liquid from the reservoir into the injection site through the needle.

The syringe according to the present invention addresses the problems associated with conventional syringes in a number of respects. Firstly, it causes the needle to be deployed automatically and the gas generator to be actuated automatically by pressing the sleeve against the skin and moving the barrel relative to the sleeve (e.g. as part of one movement in which the barrel is gripped and pressed, sleeve first, against the skin).

Because the penetration of the needle is controlled by the extent of movement of the components of the syringe, incorrect injection is less likely. Furthermore, because the gas generator itself causes the delivery of the drug, the speed and amount of delivery are predetermined and out of the control of the user. Automatic delivery also prevents needle injuries from occurring as a result of the user having to manipulate the syringe during the time when the needle is penetrating the skin.

Needle injuries are further prevented because the sleeve conceals the needle when in the first position. Not only does this prevent accidental injury, but it also addresses user compliance problems. It is the experience of many doctors and nurses that many patients are prepared to have injections administered but will close their eyes or turn their heads during injection. For such patients it is not the actual pain of injection, but rather the sight of the injection taking place or the sight of the needle itself, which causes distress.

In cases where a patient cannot watch an injection taking place, self-injection is not practical. The syringe according to the invention provides a solution, since not only does it allow the needle to remain invisible during delivery, but it allows the patient to self-inject without looking at the needle at all.

In contrast to needleless syringes, the syringe according to the present invention does not require a significant amount of pressure to deliver the drug as the needle pierces the outer layers of skin enabling the liquid drug to flow subcutaneously at relatively low pressure. As a result, the present invention does not require pre-pressurised chambers since a relatively simple gas generator creating a relatively low pressure can be employed. The syringe according to the present invention can be sold and safely stored for extended periods of time in a pre-filled condition which ensures sterility.

Because the present invention is automatically injected no priming is required on the part of the user, and correct depth of delivery is ensured consistently.

Suitably, the gas generator is disposed at an end of the reservoir distal from the needle, and wherein the relative movement of the sleeve and the barrel cases the gas generator to be compressed and thereby actuated.

The arrangement of the gas generator at the second end of the barrel provides a compact syringe, not significantly bigger than a conventional syringe. Indeed, the size of the syringe according to the invention may be significantly smaller than a conventional prefilled syringe having the same delivery volume. This is because in such syringes the plunger is extended before use, almost doubling the syringe length. Such size reductions are advantageous because storage costs and transportation costs are reduced and convenience increased.

Suitably, the gas generator comprises first and second chambers separated by a deformable membrane.

Preferably, the gas activation means comprises means for puncturing the deformable membrane.

In preferred embodiments, the gas activation means is activated by movement of the barrel and sleeve from the first position to the second position.

The advantage of the arrangement of the present invention is that the syringe operates to reliably inject a substance with the user being only required to press the barrel, sleeve first, towards the injection site. This single movement serves to penetrate the skin and activate the gas generator, causing the drug to be injected. Thus, the number of steps involved is not only fewer than in the prior art alternatives to conventional syringes, but also fewer even than for conventional pre-filled syringes.

With a pre-filled syringe, the user (or physician or nurse) must first penetrate the injection site with the needle, and second, depress the plunger to deliver the drug. Both of these steps may be relatively simple to a trained person, but they nevertheless each require considerable care. According to the present invention, however, the barrel can be grasped, pushed against the skin and removed after delivery. No other steps are required and no particular care needs to be taken because the automatic nature of the device removes the likelihood of user error.

Preferably, the sleeve is axially biased towards the first position so that it moves to the first position when no pressure is applied to the barrel.

This feature ensures that the needle is never visible to the user and obviates the need for the user to employ a retraction mechanism. This feature improves the safety of the syringe and reduces the likelihood of injury if the syringe is not disposed of properly.

Many healthcare workers accidentally prick themselves each year in hospitals and clinics throughout the world. Such accidents may result in the contraction of a fatal disease or considerable mental anguish associated with the possibility of contracting a fatal disease. As a result of these risks, hospitals and other healthcare providers are continually seeking ways to decrease the risk of injury associated with exposed, contaminated needles. The present invention addresses this problem and reduces the risk of injury by employing syringes in which the needle is automatically retracted. Healthcare organisations and institutions could lower the occurrence of such injuries and also lower their liability for such claims against them by healthcare workers and significantly reduce injury and illness as well as insurance premiums.

Preferably, the sleeve is axially biased by means of a coil spring.

Further, preferably, the coil spring is disposed between the sleeve and the barrel. A coil spring disposed in this way does not add to the size of the syringe.

Preferably, the sleeve is torsionally biased. Such torsional biasing enables advantageous safety features to be achieved, as will be explained further below.

Suitably, the axial and torsional bias are provided by a compression-extension spring under torsional strain.

The compression-extension spring may be a coil spring disposed between the sleeve and the barrel. A coil spring disposed in this way does not add to the size of the syringe, but it adds the safety feature of a permanently concealed needle, and a safety locking mechanism as described below.

Preferably, the syringe further comprises locking means such that when the sleeve from returns from the second position to the first position the locking means prevents the sleeve from returning to the second position.

This feature provides a single use syringe which can be safely disposed of without fear of accidental injury. Even if not correctly disposed of, the fact that the sleeve becomes locked after use in the second position means that the needle is permanently concealed by the sleeve to prevent accidental injury and to deter intentional re-use of the syringe.

Preferably, the locking means comprises a pair of co-operating formations disposed on the sleeve and the barrel respectively.

Further, preferably, the pair of co-operating formations comprises a slot and a member received in the slot respectively.

A suitably shaped slot has an angled portion which causes the rotational biasing to increase as the sleeve completes its travel from the second position back to the first position, and a horizontal portion (perpendicular to the axis of the barrel) which permits rotational relaxation when the sleeve has returned to the first position.

Preferably, the first and second chambers house the components of an effervescent couple respectively.

A large volume of gas can be generated from a relatively small quantity of solid or liquid effervescent reactants. Thus, the size of the gas generator can be significantly smaller than the volume of liquid to be delivered, and for this reason, the syringe according to the invention may be made of a size comparable to conventional syringes.

Preferably, at least one of the components of the couple is a liquid.

Further, preferably, the components of the effervescent couple are citric acid and sodium bicarbonate respectively.

The cost of an effervescent couple (such as citric acid and sodium bicarbonate) is relatively low and so the mechanism employed is extremely inexpensive compared to that of a compressed gas needleless injector.

Preferably, the needle extends between about 1–3 mm beyond the first end of the barrel.

Once the stratum corneum has been penetrated, subcutaneous delivery can be easily achieved. Thus, there is no necessity for a deep penetration.

Most preferably, the needle extends approximately 1 mm beyond the first end of the barrel.

Because the injection site is already stretched by the sleeve (to which pressure is applied in order to cause movement between the first and second positions), the syringe according to the invention enables a very small depth of penetration to be achieved. With conventional syringes, the natural elasticity of the skin makes it difficult to ensure a small penetration depth: the force applied to the needle tip in order to overcome the elasticity of the skin causes the needle to penetrate deeper than necessary once the skin is penetrated.

Another factor related to the penetration of the skin is the direction of penetration. In order to prevent excessive pain, the orientation of the needle into the skin should not vary at all. If there is any movement of the needle, the entry wound becomes enlarged.

The device according to the invention has a short needle which always penetrates at 90° to the skin surface against which the sleeve abuts. Because the skin is stretched by the sleeve, small movements of the barrel or changes in direction do not cause any movement of the stretched skin surface relative to the sleeve, and hence to the needle also.

Preferably the gas generator generates a pressure of about 2 atmosphere.

Such a pressure delivers a liquid at an acceptable rate into the tissue immediately below the epidermis.

The invention also provides a method of injecting liquid drug comprising the following steps:

a) providing a barrel having a liquid drug reservoir therein, a delivery needle mounted on the first end of the barrel, b) locating a gas generator at the second end of the barrel, the gas generator in communication with the reservoir when the gas generator is activated, so as to drive a liquid from the reservoir through the needle;

c) resiliently mounting a sleeve within the first end of barrel, the sleeve capable of assuming a first position where the tip of the needle is concealed by the sleeve and a second position where the tip of the needle is revealed;

d) activating the gas generator;

e) placing the sleeve against an injection site; and f) moving the barrel toward the injection site, thereby causing the sleeve to move from the first position to the second position, the needle to penetrate the injection site, and the gas generator to drive a liquid from the reservoir into the injection through the needle.

Preferably, the method according to the invention further comprises the step of causing the sleeve to return to the first position after moving to the second position.

Further, preferably, the method further comprises the step of preventing the sleeve from returning to the second position after returning to the first position.

The invention will be further illustrated by the following description of embodiments thereof, given by way of example only with reference to the accompanying drawings, in which:

FIG. 1 is a sectional view of a syringe according to the invention, illustrated as supplied to the user;

FIG. 2 is an exploded view of the syringe of FIG. 1;

FIG. 3 is a sectional view of the syringe of FIG. 1, with the needle cover removed;

FIG. 4 is a sectional view of the syringe of FIG. 1, shown as it is being applied to the injection site;

FIGS. 7A–7D are sectional views of a detail of the syringe of FIG. 1, shown at successive stages corresponding to FIGS. 3–6, respectively;

FIG. 8 is a perspective view of a spring used in the syringe of FIG. 1;

FIG. 9 is a perspective view of the syringe of FIG. 1; and

Figures 5, 6:
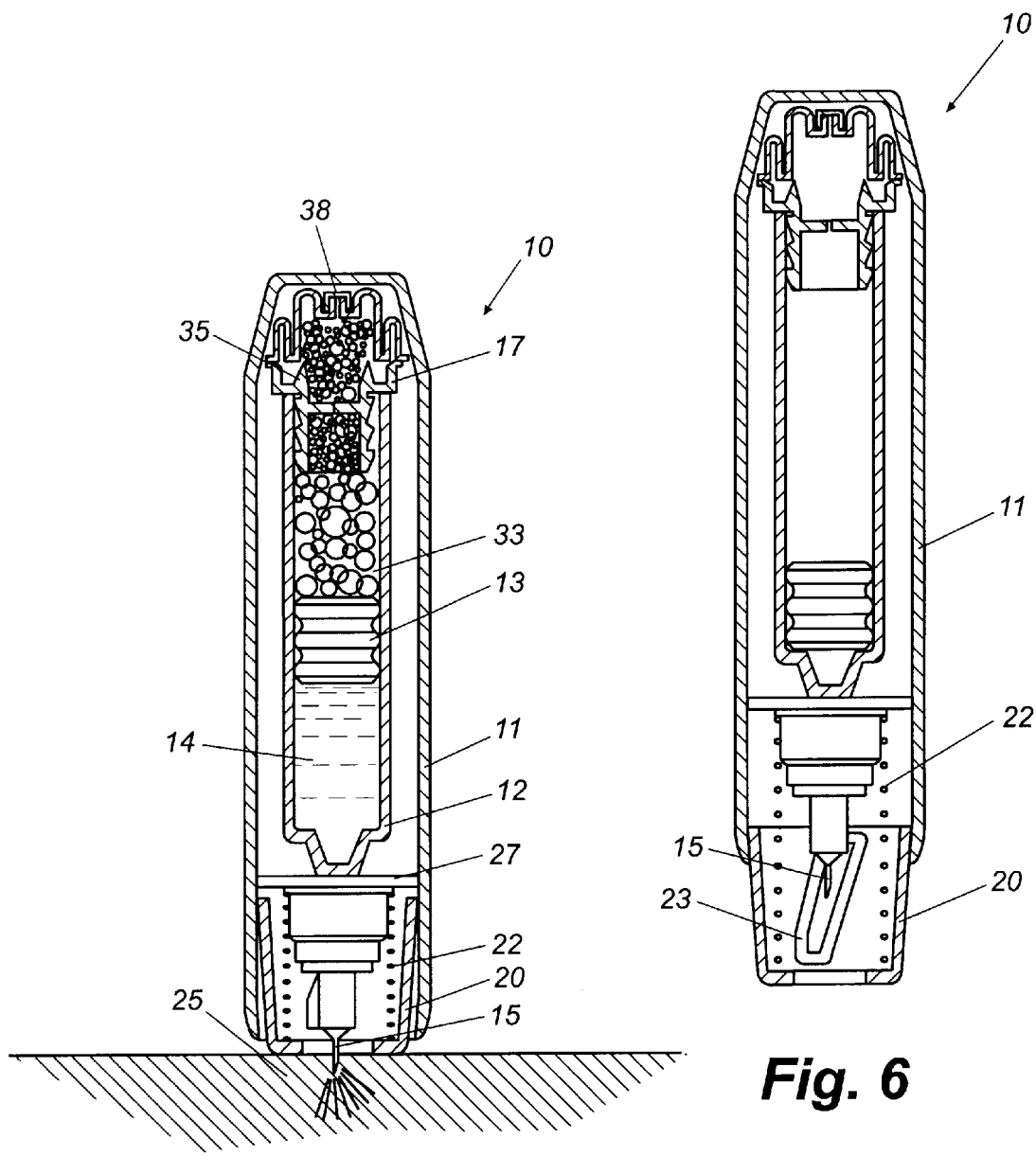
FIG. 5 is a sectional view of the syringe of FIG. 1, shown as the liquid is being injected.
FIG. 6 is a sectional view of the syringe of FIG. 1, shown after injection.

In FIG. 1 there is indicated, generally at 10, a syringe according to the invention which is shown in exploded view in FIG. 2. The syringe 10 comprises a barrel 11 containing an internal cylindrical body 12 in which a piston 13 is slidably inserted. A reservoir for a liquid 14 for injection is defined on one side of piston 13 within cylindrical body 12. A needle 15 is mounted on a mounting body 28 which joins the needle to a first end of the cylindrical body 12. The internal cylindrical body 12 communicates with the liquid 14 and enables delivery thereof under movement by the piston 13. For sterility the needle 15 is protected by a protective cover 16 before use.

A gas generator 17 is mounted within the barrel 11 at the opposite end of the cylindrical body 12 from the needle 15. The generator 17 is provided with a plug fitting 18 which is received by the cylindrical body 12. A displaceable sleeve 20 is mounted at the opposite, open end 19 of the barrel 11. The sleeve 20 has an aperture 21 through which the needle cover 16 protrudes before use. The sleeve 20 is movable from the first position shown in FIGS. 1 and 2 by sliding upwards in the interior of barrel 11, as will be described further below. However, a coil spring 22 biases the sleeve 20 to the first position as shown in FIG. 1.

FIG. 2 shows a shaped slot 23 in the sleeve 20 which, when assembled, receives a peg 24 in the interior of the barrel 11. The shape of the slot 23 causes relative rotation between the barrel 11 and the sleeve 20 when they are moved axially relative to one another. This feature, which provides a safety locking mechanism, will be explained in greater detail below.

FIG. 3 shows the syringe 10 immediately before use. The needle cover 16 is removed by the user by pulling it away from the barrel 11 out of the aperture 21. It can be seen that even in this configuration, wherein the syringe 10 is ready for use, the needle 15 is concealed by the sleeve 20.

In order to use syringe 10, the sleeve 20 is placed against an injection site 25 as shown in FIG. 4, and barrel 11 is pushed against the injection site 25. The freedom of movement of the sleeve 20 enables the barrel 11 to move downwardly towards the injection site 25, with the sleeve 20 being received internally of the barrel 11. In FIG. 4, the syringe is shown just before the sleeve 20 has reached its limit of internal movement, i.e. just before the second position referred to above. At this point, the upper lip 26 of the sleeve 20 is abutting against a flange 27 of mounting body 28 which mounts the needle 15 on the cylindrical body 12. It can be seen that the needle 15 has penetrated the injection site 25.

The gas generator 17, however, has not yet been actuated. The gas generator 17 comprises an upper chamber 29 filled with citric acid solution 30 and a lower chamber 31 containing a mass of sodium bicarbonate 32 (other effervescent couples could of course be used). A lower chamber 31 communicates with a pumping chamber 33 in cylindrical body 12 defined between the gas generator 17 and the piston 13.

Upper chamber 29 is bounded by a penetrable laminated foil membrane 34. A cutting member 35 is provided in the lower chamber 31 so as to rest against the membrane 34. The membrane 34 must create a barrier between the upper and lower chambers 29,31 yet be penetrable. The upper and lower chambers 29,31 are connected together by a circumferential seal 36.

The upper chamber 29 is provided with a flexible peripheral portion 37 adjacent to the seal 36. Because of its flexibility, the peripheral portion 37 imparts a small amount of freedom of movement of upper chamber 29 towards lower chamber 31. Therefore, if the gas generator 27 is mechanically compressed, the upper chamber 29 moves towards the lower chamber 31 resulting in the penetration of the foil membrane 34 by the cutting member 35.

Downward pressure on the barrel 11 results in the situation shown in FIG. 5. The sleeve 20 pushes the flange 27 and hence the cylindrical body 12 and the gas generator 17 upwards within the barrel 11. When the gas generator 17 reaches the top of barrel 11 it is compressed. This compression causes cutting member 35 to penetrate foil membrane (not visible in FIG. 5), releasing citric acid 30 into contact with sodium bicarbonate 32. This results in the immediate generation of carbon dioxide causing the pumping chamber 33 to become pressurised, which in turn drives the piston 13 downwards to deliver the liquid 14 from cylindrical body 12 to the injection site 25 via the needle 15.

When delivery has been completed (this may suitably take of the order of 3–5 seconds, although longer or shorter times can be achieved if required), gas generation will generally not have been completed: a surplus of reactive gas generating materials is provided so as to ensure completion of delivery. In order to prevent any dangerous pressure build up a release valve 38 is provided on the gas generator 17. The release valve 38 opens when pressure reaches a predetermined level. Thus, release valve 38 is also actuated by any blockage in delivery.

When delivery has been completed, the barrel 11 is removed from the injection site 25. As the pressure on the barrel 11 is relieved, the spring 22 pushes the sleeve 20 from the second position (FIG. 5) back to the first position (FIG. 6). Thus, the needle 15 is concealed even before the sleeve 20 has left the injection site 25. For severely needlephobic patients, any sight of the needle must be avoided if possible, and for safety reasons, it is highly preferable that the needle is never exposed. As a result of the slot 23 and the location of the peg 24 in the first position (as shown in FIG. 7D), the sleeve 20 is locked in the first position when it returns from the second position and the pressure of the spring 22 prevent it from returning to the second position, as will be discussed in more detail below.

FIGS. 7A–7D illustrate the operation of the safety locking mechanism by showing the position of the peg 24 (mounted in the interior of barrel 11) in the slot 23 formed in the sleeve 20, at four stages of the delivery procedure, with FIGS. 7A–7D corresponding to FIGS. 3–6, respectively.

As indicated previously, the sleeve 20 is biased to the first position (FIGS. 3 and 7A) by a coil spring 22, illustrated in FIG. 8. The ends of spring 22 form two outward projections 39, one of which engages barrel 11 and the other of which engages the sleeve 20. In addition to providing an axial biasing, spring 22 rotationally biases the sleeve 20 relative to the barrel 11 towards an equilibrium position, but the slot 23 and peg 24 constrain the relative rotation of the barrel 11 and the sleeve 20.

The equilibrium position is indicated in FIGS. 7A–7D by a dotted line, which is the equilibrium position of the peg 24 in barrel 11 relative to the sleeve 20. Accordingly, in FIGS. 7A–7C the peg 24 is to the left of the relaxed equilibrium position (in the view shown), resulting in a rotational bias of the sleeve 20 relative to the barrel 11 which would cause the peg to move to the right. In FIG. 7D, the peg is effectively at the equilibrium position.

As the peg 24 is constrained in the slot, it has to follow the path illustrated in FIGS. 7A–7C as the sleeve moves from the first position (FIG. 7A) to the second position (FIG. 7C). When delivery is completed and the pressure on the barrel is released, the sleeve is axially moved from the second position (FIG. 7C) to the first position. The rotational biasing of the spring 22, however, causes the peg 24 to travel into the right-hand arm 40 of the slot 23 (FIG. 7C), rather than the left-hand arm 41 in which it started. When the sleeve 20 has moved most of the way back towards the first position (just before the point illustrated in FIG. 7D), the peg 24 is biased to move leftwards (as seen in the view of FIGS. 7A–7D) and passes the top right-hand corner 42 of the slot 23. At this point the peg is free to move leftwards, and thus it springs to the position shown in FIG. 7D, i.e. the barrel 11 and the sleeve 20 rotate relative to one another under the influence of the spring 22 to reach the FIG. 7D position.

When the peg 24 is in the position shown in FIG. 7D it is effectively trapped, and any attempt to move the sleeve 20 axially relative to the barrel 11 results in the peg 24 being stopped in the small notch 43. Accordingly, after a single reciprocation from the first position to the second position and back to the first position, the sleeve 20 is locked and the needle 22 is permanently concealed.

FIG. 9 shows the syringe 10 in perspective view before use. Thus, barrel 11, sleeve 20, and needle cover 16 can be seen. Also visible are slot 23 and the position of pin 24. A further feature is a transparent window 44 which allows the user to see when the delivery of liquid is complete so that the syringe 10 can be removed.

The needle 15 is preferred to extend from the sleeve by 1–3 mm, most preferably by 1 mm in length. In addition the ratio of citric acid to sodium bicarbonate in the gas generator should be sufficient to preferably generate a delivery pressure of approximately 2 atmospheres. This enables the syringe 10 to deliver the liquid 14 to the user automatically at a low pressure and with a reduced risk of injury.

Figure 10:
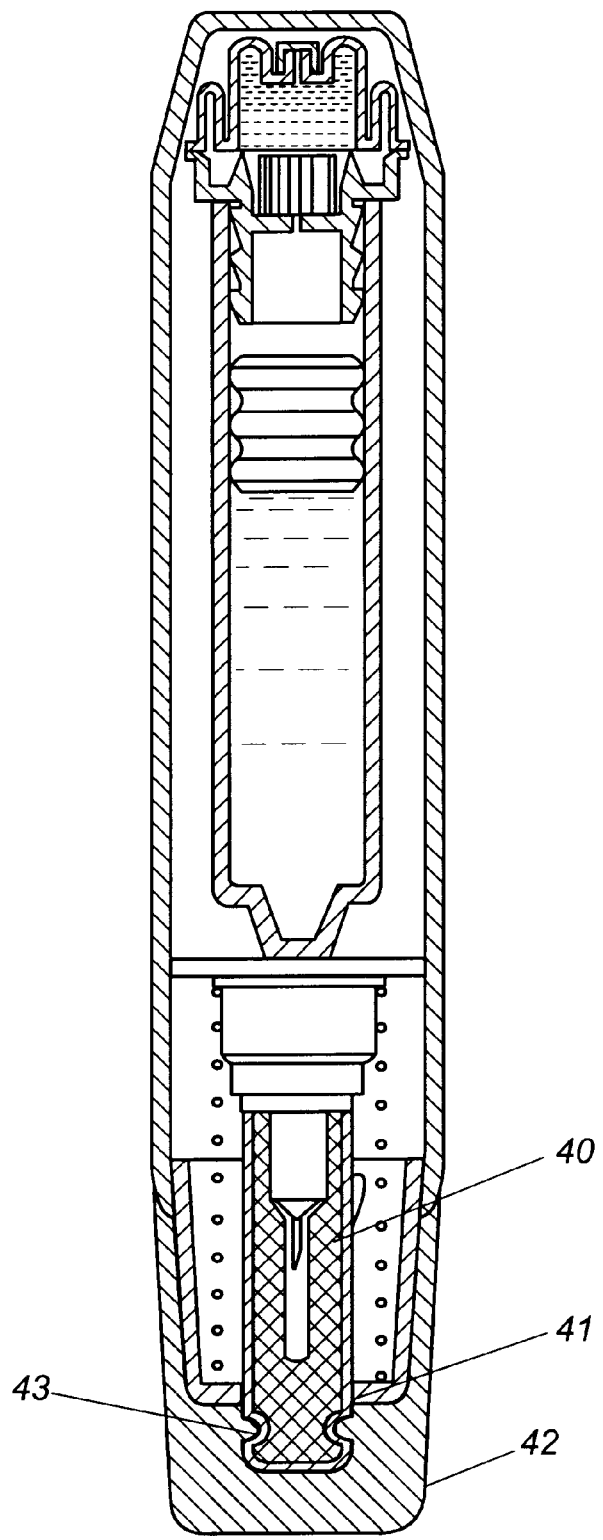
FIG. 10 is a sectional view of a first alternative embodiment of the present invention.

FIG. 10 shows a first alternative embodiment of the present invention. It is similar to the syringe described in detail above except that it has a needle cover different from that shown in FIG. 1. FIG. 10 shows a needle cover 40 shaped to fit over the needle 15. The needle cover also has a radial groove 41 located at the opposed end of the needle on the exterior of the cover. The needle cover 40 and sleeve 20 are covered by a cap 42. The cap 42 has an interior groove 43 that matingly receives the radial groove of the needle cover 40 when the cap is placed over the needle cover 40 and sleeve 20. The cap 42 maintains the sterility of the needle 15 until removal of the cap. When the cap 42 is pulled off the syringe prior to use, the mating pair of grooves cause the needle cover 40 to be pulled off at the same time. When the cap 42 is placed back over the sleeve 20, the needle cover 40 is also placed over the needle 15 to further avoid contamination and/or leakage of any remaining residue left within the syringe 10.

Figure 11:
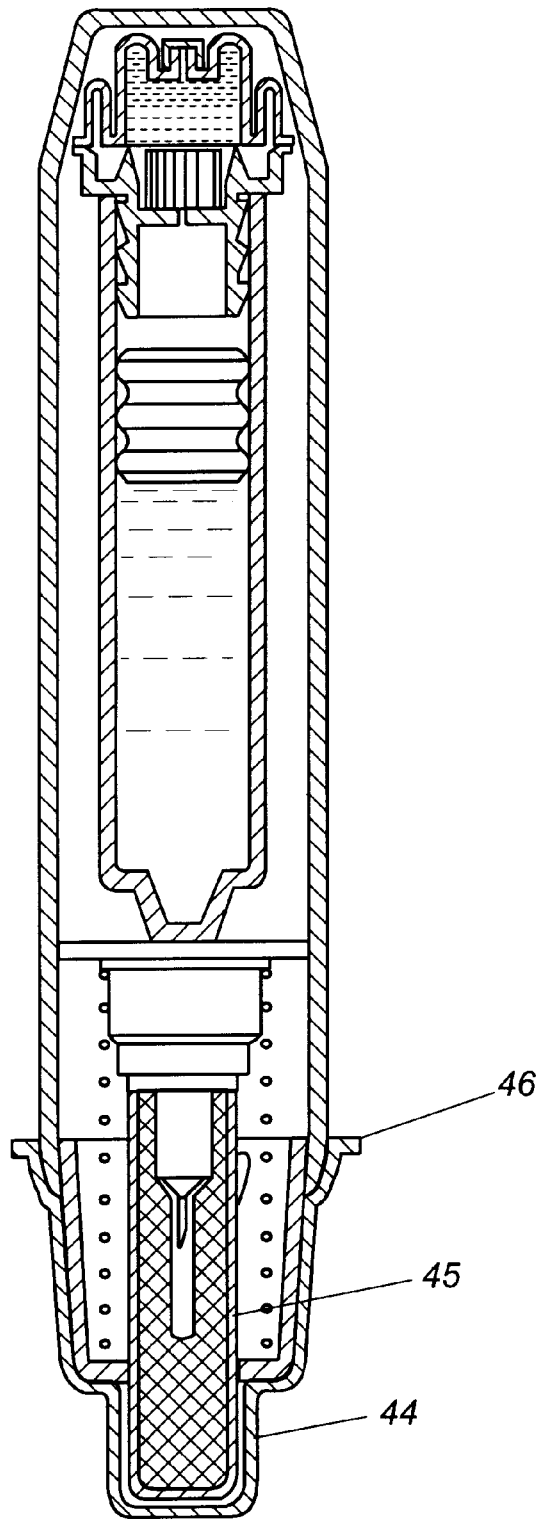
FIG. 11 is a sectional view of a second alternative embodiment of the present invention.

FIG. 11 shows a second alternative embodiment of the present invention. FIG. 11 is similar to the embodiment shown in FIG. 10 but has a different cap 44 and needle cover 45. The cap 44 has an outer lip 46 that rests over the open end 19 of the barrel 11. The needle cover 45 is cylindrical in shape and covers the needle 15 and maintains its sterility until use. Prior to use, the user must first remove the cap 44, and then remove the needle cover 45. After use, the user must replace the needle cover 45 and then the cap 44 separately.

It will be appreciated that the embodiments discussed above are preferred embodiments, falling within the scope of the appended claims, and that various alternative embodiments are contemplated.

For example, other chemically reactive materials other than citric acid and sodium bicarbonate may be used in connection with the gas generator of the present invention. Other mechanisms other than the coil spring 22 may be used to exert upward pressure on the barrel 11 and activate the gas generator 17. Such alternative mechanisms include the use of any elastic or resilient member.

It is further appreciated that the present invention may be used to deliver a number of drugs. The term "drug" used herein includes but is not limited to peptides or proteins, hormones, analygesics, anti-migratine agents, anti-coagulant agents, narcotic antagonists, chelating agents, anti-anginal agnets, chemotherapy agents, sedatives, anti-neoplasticws, prostaglandins and antidiuretic agents.

Typical drugs include peptides, proteins or hormones such as insulin, calcitonin, calcitonin gene regulating protein, atrial natriuretic protein, colony stimulating factor, betaseron, erythrogpoietin (EPO), interferons suchs as α, β or γ interferon, somatropin, somatotropin, somastostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor viii, interleukins such as interleukin-2, and analogues therof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues therof; anti-coagulant angents such as heparin, hirudin, and anlogues therof; anti-emetic angets such as scopolamine, ondansetron, domperidone, metoclopramide,a nd analogues thereof; cardiovascular agents, anti-hypertensive agents and vasodilators such as diltiazem, clonidine, nifedipine, varapmil, isosorbide-5-mononitrate, organic nitrates, agents used in treatment of heart disorders, and analogues thereof; sedatives such as benzodiazepines, phenothiozines, and analogues thereof; chelating agents such as deferoxamine, and anlogues thereof; anti-diuretic agents such as desmopressin, vasopressin, and anlogues thereof; anti-anginal agents such as nitroglycerine, and analogues thereof; anti-neoplastics such as fluorouracil, bleomycin, and analogues thereof; prostaglandins and analogues thereof; and chemotherapy agents such as vincristine, and analogues thereof.

What is claimed is:

1. A syringe comprising:
   a) a barrel having a liquid drug reservoir therein, the barrel having a first end and a second end;
   b) a delivery needle mounted on the first end of the barrel;
   c) a gas generator located at the second end of the barrel, the gas generator in communication with the reservoir when the gas generator is activated;
   d) gas generation activation means; and
   e) a sleeve moveably mounted on the first end of the barrel from a first position where the tip of the needle is concealed by the sleeve to a second position where the tip of the needle is exposed to a third gas generation activation position,
   f) whereby when the sleeve is initially pressed against an injection site, the sleeve moves from the first position to the second position, and the tip of the needle penetrates the injection site, and when the sleeve moves from the second position to the third position, it causes activation of the gas generator which drives a liquid from the reservoir into the injection site through the needle.

2. The syringe of claim 1 wherein the gas generator comprises first and second chambers separated by a deformable membrane.

3. The syringe of claim 2 wherein the gas activation means comprises means for puncturing the deformable membrane.

4. The syringe of claim 2 wherein the first and second chambers house the components of an effervescent couple respectively.

5. The syringe of claim 4 wherein at least one of the components of the couple is a liquid.

6. The syringe of claim 4 wherein the components of the effervescent couple are citric acid and sodium bicarbonate respectively.

7. The syringe of claim 1 wherein the gas activation means is activated by movement of the barrel and sleeve from the first position to the second position.

8. The syringe of claim 1 wherein the sleeve is axially biased towards the first position so that it moves to the first position when no pressure is applied to the barrel.

9. The syringe of claim 8 wherein the sleeve is axially biased by means of a coil spring.

10. The syringe of claim 9 wherein the coil spring is disposed between the sleeve and the barrel.

11. The syringe of claim 5 wherein the sleeve is torsionally biased.

12. The syringe of claim 11 wherein the axial and torsional bias are provided by a compression-extension spring under torsional strain.

13. The syringe of claim 1 further comprising locking means such that when the sleeve returns from the second position to the first position the locking means prevents the sleeve from returning to the second position.

14. The syringe of claim 13 wherein the locking means comprises a pair of co-operating formations disposed on the sleeve and the barrel respectively.

15. The syringe of claim 14 wherein the pair of co-operating formations comprises a slot and a member received in the slot respectively.

16. The syringe of claim 1 wherein the needle extends between about 1–3 mm beyond the first end of the barrel.

17. The syringe of claim 1 wherein the needle extends approximately 1 mm beyond the first end of the barrel.

18. The syringe of claim 1 wherein the gas generator generates a pressure of about 2 atmosphere.

19. A method of injecting liquid drug comprising the following steps:
   a) providing a barrel having a liquid drug reservoir therein, a delivery needle mounted on the first end of the barrel,
   b) locating a gas generator at the second end of the barrel, the gas generator in communication with the reservoir when the gas generator is activated;

c) moveably mounting a sleeve within the first end of the barrel, the sleeve capable of assuming a first position where the tip of the needle is concealed by the sleeve, a second position where the tip of the needle is revealed, and a third gas generator activation position;

d) placing the sleeve against an injection site;

e) moving the barrel toward the injection site, thereby causing the sleeve to move from the first position to the second position and the tip of the needle to penetrate the injection site; and f) moving the sleeve to the third position to activate the gas generator thereby driving a liquid from the reservoir into the injection site through the needle.

20. The method of claim 19 further comprising the step of causing the sleeve to return to the first position after moving to the second position.

21. The method of claim 20 further comprising the step of preventing the sleeve from returning to the second position after returning to the first position.

22. The method of claim 19 wherein the gas generator comprises a first chamber and a second chamber separated by a deformable membrane.

23. The method of claim 22 wherein the first and second chambers house the components of an effervescent couple respectively.

24. The method of claim 23 wherein at least one of the components of the couple is a liquid.

25. The method of claim 23 wherein the components of the effervescent couple are citric acid and sodium bicarbonate respectively.

26. The method of claim 22 the gas generator is activated by piercing the membrane.

27. The method of claim 19 wherein the needle penetrates the injection site about 1–3 mm.

28. The method of claim 19 wherein the pressure within the gas generator is about 2 atmosphere.

29. A syringe comprising:

a member having a liquid drug reservoir therein, the member having a first end and a second end;

a delivery needle mounted on the first end of the member;

a gas generator located at the second end of he member, the gas generator in communication with the reservoir when the gas generator is activated; and a sleeve moveably mounted on the first end of the member from a first position where the tip of the needle is enclosed by the sleeve, to a second position where the tip of the needle is exposed, to a third position where the sleeve activates the gas generator, whereby when the sleeve is initially pressed against an injection site, the sleeve moves from the first position to the second position, and the tip of the needle penetrates the injection site, and when the sleeve moves from the second position to the third position, it causes activation of the gas generator which drives a liquid from the reservoir into the injection site through the needle.

30. A method of injecting liquid drug comprising the following steps:

a) providing a member having a liquid drug reservoir therein, a delivery needle mounted on the first end of the member, b) locating a gas generator at the second end of the member, the gas generator in communication with the reservoir when the gas generator is activated;

c) moveably mounting a sleeve within the first end of the member, the sleeve capable of assuming a first position where the tip of the needle is concealed by the sleeve, a second position where the tip of the needle is revealed, and a third position where the gas generator is activated;

d) pressing the sleeve against an injection site, thereby causing the sleeve to move from the first position to the second position and the tip of the needle to penetrate the injection site; and e) moving the sleeve to the third position to activate the gas generator, thereby driving the liquid from the reservoir into the injection site through the needle.

* * * * *

UNITED STATES PATENT AND TRADEMARK OFFICE
CERTIFICATE OF CORRECTION

PATENT NO. : 6,099,504
DATED : August 8, 2000
INVENTOR(S) : Joseph Gross et al.

It is certified that error appears in the above-identified patent and that said Letters Patent is hereby corrected as shown below:

<u>Title page,</u>
Item [63], insert:
-- [63]          Related U.S. Application Data
Provisional Application No. 60/135,509, filed on October 20, 1998 which was converted from utility application No. 08/956,237 filed on October 22, 1997. --

Signed and Sealed this

Ninth Day of September, 2003

JAMES E. ROGAN
*Director of the United States Patent and Trademark Office*